United States Patent
Schoentjes et al.

(10) Patent No.: US 6,624,164 B2
(45) Date of Patent: Sep. 23, 2003

(54) 1,3-DIHYDRO-2H-INDOL-2-ONE DERIVATIVES, PREPARATION METHOD AND PHARMACEUTICAL COMPOSITION CONTAINING THEM

(75) Inventors: Bruno Schoentjes, Strasbourg (FR); Claudine Serradeil-Le Gal, Escalquens (FR); Jean Wagnon, Montpellier (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 10/182,638

(22) PCT Filed: Jan. 24, 2001

(86) PCT No.: PCT/FR01/00228
§ 371 (c)(1),
(2), (4) Date: Nov. 25, 2002

(87) PCT Pub. No.: WO01/55134
PCT Pub. Date: Aug. 2, 2001

(65) Prior Publication Data
US 2003/0139413 A1 Jul. 24, 2003

(30) Foreign Application Priority Data
Jan. 25, 2000 (FR) .............................................. 00 00958

(51) Int. Cl.[7] ........................ A61K 31/5377; A61P 9/12; C07D 413/04
(52) U.S. Cl. ..................................... 514/235.2; 544/144
(58) Field of Search .......................... 544/144; 514/235.2

(56) References Cited

U.S. PATENT DOCUMENTS

| 5,397,801 A | 3/1995 | Wagnon et al. |
| 5,594,023 A | 1/1997 | Wagnon et al. |
| 5,773,612 A | 6/1998 | Wagnon et al. |
| 6,090,818 A | 7/2000 | Foulon et al. |

FOREIGN PATENT DOCUMENTS

| WO | WO 95/18105 | 7/1995 |
| WO | WO 98/25901 | 6/1998 |

*Primary Examiner*—Robert W. Ramsuer
(74) *Attorney, Agent, or Firm*—Paul E. Dupont; Michael D. Alexander

(57) ABSTRACT

The invention relates to compounds of formula:

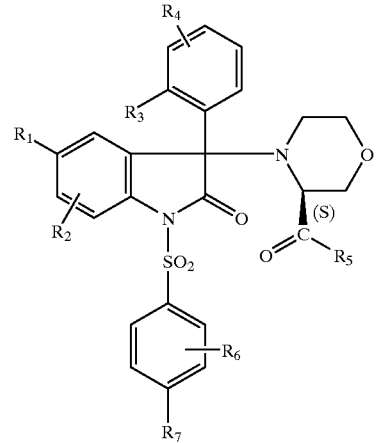

(I)

and their solvates and/or hydrates exhibiting affinity for the arginine-vasopressin $V_{1b}$ receptors or for both $V_{1b}$ and $V_{1a}$ receptors.

The invention also relates to their process of preparation, to the intermediate compounds of formula (II) of use for their preparation, to the pharmaceutical compositions comprising them and to their use for the preparation of medicaments.

24 Claims, No Drawings

1,3-DIHYDRO-2H-INDOL-2-ONE DERIVATIVES, PREPARATION METHOD AND PHARMACEUTICAL COMPOSITION CONTAINING THEM

A subject of the present invention is novel 1,3-dihydro-2H-indol-2-one derivatives, a process for their preparation and the pharmaceutical compositions comprising them.

The compounds according to the present invention exhibit an affinity and a selectivity for arginine-vasopressin (AVP) $V_{1b}$ receptors or for both $V_{1b}$ and $V_{1a}$ receptors.

AVP is a hormone known for its antidiuretic effect and its effect in regulating arterial pressure. It stimulates several types of receptors: $V_1$ ($V_{1a}$, $V_{1b}$) or $V_2$. These receptors are located in particular in the liver, vessels (coronary, renal, cerebral), platelets, kidney, uterus, adrenal glands, pancreas, central nervous system or pituitary gland. AVP thus exerts cardiovascular, hepatic, pancreatic, antidiuretic and platelet-aggregating effects and effects on the central and peripheral nervous system and on the uterine sphere.

The localization of various receptors is described in: S. Jard et al., Vasopressin and oxytocin receptors: an overview, in Progress in Endocrinology, H. Imura and K. Shizurne ed., Experta Medica, Amsterdam, 1988, 1183–1188, and in the following articles: J. Lab. Clin. Med., 1989, 114 (6), 617–632 and Pharmacol. Rev., 1991, 43 (1), 73–108.

More particularly, AVP $V_{1a}$ receptors are located in numerous peripheral organs and in the brain. They have been cloned in the rat and man and they regulate the majority of known effects of AVP: platelet aggregation; uterine contractions; vessel contraction; the secretion of aldosterone, of cortisol, of CRF (corticotropin-releasing factor) and of adrenocorticotrophic hormone (ACTH); hepatic glycogenolysis, cell proliferation and the main central effects of AVP (hypothermia, memory, and the like).

The $V_{1b}$ receptors were initially identified in the adenohypophysis of various animal species (rat, pig, cow, sheep, and the like), including in man (S. Jard et al., Mol. Pharmacol., 1986, 30, 171–177; Y. Arsenijevic et al., J. Endocrinol., 1994, 141, 383–391; J. Schwartz et al., Endocrinology, 1991, 129 (2), 1107–1109; Y. de Keyser et al., FEBS Letters, 1994, 356, 215–220), where they stimulate the release of adrenocorticotrophic hormone by AVP and potentiate the effects of CRF on the release of ACTH (G. E. Gillies et al., Nature, 1982, 299, 355). In the hypothalamus, the $V_{1b}$ receptors also induce a direct release of CRF (Neuroendocrinology, 1994, 60, 503–508) and are, in these various respects, implicated in stress situations.

These $V_{1b}$ receptors have been cloned in the rat, man and mouse (Y. de Keyser, FEBS Letters, 1994, 356, 215–220; T. Sugimoto et al., J. Biol. Chem., 1994, 269 (43), 27088–27092; M. Saito et al., Biochem. Biophys. Res. Commun., 1995, 212 (3), 751–757; S. J. Lolait et al., Neurobiology, 1996, 92, 6783–6787; M. A. Ventura et al., Journal of Molecular Endocrinology, 1999, 22, 251–260) and various studies (in situ hybridization, PCR (Polymerase Chain Reaction), and the like) reveal ubiquitous localization of these receptors in various central tissues (brain, hypothalamus and adenohypophysis, in particular) and peripheral tissues (kidney, pancreas, adrenal glands, heart, lungs, intestine, stomach, liver, mesentery, bladder, thymus, spleen, uterus, retina, thyroid, and the like) and in some tumors (hypophyseal or pulmonary tumors, and the like), suggesting a broad biological and/or pathological role of these receptors and potential involvement in various diseases.

By way of examples, in the rat, studies have shown that AVP, via the $V_{1b}$ receptors, regulates the endocrine pancreas, stimulating the secretion of insulin and of glucagon (B. Lee et al., Am. J. Physiol., 269 (Endocrinol. Metab. 32), E1095–E1100, 1995) or the production of catecholamines in the medulloadrenal, which is the site of a local synthesis of AVP (E. Grazzini et al., Endocrinology, 1996, 137 (a), 3906–3914). Thus, in the last tissue, AVP, via these receptors, would have a crucial role in some types of adrenal pheochromocytomas which secrete AVP and which, for this reason, bring about a sustained production of catecholamines which are the cause of hypertensions which are resistant to angiotensin-II receptor antagonists and to converting enzyme inhibitors. The adrenal cortex is also rich in $V_{1a}$ receptors involved in the production of gluco- and mineralocorticoids (aldosterone and cortisol). $V_{1a}$ these receptors, AVP (circulating or synthesized locally) can bring about production of aldosterone with an effectiveness comparable to that of angiotensin II (G. Guillon et al., Endocrinology, 1995, 136 (3), 1285–1295). Cortisol is a powerful regulator of the production of ACTH, the stress hormone.

Recent studies have also shown that the adrenal glands are capable of directly releasing CRF and/or ACTH via the activation of the $V_{1b}$ and/or $V_{1a}$ receptors carried by the cells of the medulla (G. Mazzocchi et al., Peptides, 1997, 18(2), 191–195; E. Grazzini et al., J. Clin. Endocrinol. Metab., 1999, 84 (6), 2195–2203).

The $V_{1b}$ receptors are also regarded as a label for ACTH-secreting tumors, which are some pituitary tumors and some bronchial (Small Cell Lung Cancers or SCLC), pancreatic, adrenal and thyroid carcinomas, resulting in some cases in Cushing's syndrome (J. Bertherat et al., Eur. J. Endocrinol., 1996, 135, 173; G. A. Wittert et al., Lancet, 1990, 335, 991–994; G. Dickstein et al., J. Clin. Endocrinol. Metab., 1996, 81 (8), 2934–2941). The $V_{1a}$ receptors are, for their part, a more specific label for small cell lung cancers (SCLC) (P. J. Woll et al., Biochem. Biophys. Res. Commun., 1989, 164 (1), 66–73). Thus, the compounds according to the present invention are obvious diagnostic tools and offer a novel therapeutic approach in the proliferation and detection of these tumors, at an early stage too (radiolabeling; SPECT (Single Photon Emission Computed Tomography); PET Scan (Positron Emission Tomography Scanner)).

The lavish presence of the messenger of the $V_{1b}$ receptors in the stomach and intestine suggests involvement of AVP via this receptor in the release of gastrointestinal hormones, such as cholecystokinin, gastrin or secretin (T. Sugimoto et al., Molecular cloning and functional expression of $V_{1b}$ receptor gene, in Neurohypophysis: Recent Progress of Vasopressin and Oxytocin Research; T. Saito, K. Kurokawa and S. Yoshida ed., Elvesier Science, 1995, 409–413).

1,3-Dihydro-2H-indol-2-one derivatives have been disclosed in some patent applications as ligands of the arginine-vasopressin and/or oxytocin receptors: mention may be made of patent applications WO 93/15051, EP 636 608, EP 636 609, WO 95/18105, WO 97/15556 and WO 98/25901.

To date, no nonpeptide compound having an affinity and a selectivity for arginine-vasopressin $V_{1b}$ receptors or for both $V_{1b}$ and $V_{1a}$ receptors is known.

Novel 1,3-dihydro-2H-indol-2-one derivatives have now been found which exhibit an affinity and a selectivity for arginine-vasopressin $V_{1b}$ receptors or for both $V_{1b}$ and $V_{1a}$ receptors.

These compounds can be used for the preparation of medicaments of use in the treatment or prevention of any pathology where arginine-vasopressin and/or the $V_{1b}$ receptors or both the $V_{1b}$ receptors and the $V_{1a}$ receptors are implicated, in particular in the treatment or prevention of conditions of the cardiovascular system, for example hypertension of the central nervous system, for example stress, anxiety, depression, obsessive-compulsive disorder or panic attacks of the renal system or of the gastric system and in the treatment of small cell lung cancers, of obesity of type-II diabetes of insulin resistance of hypertriglyceridemia of atherosclerosis of Cushing's syndrome; or of any pathology resulting from stress and chronic stress conditions.

Thus, according to one of its aspects, the subject of the present invention is compounds of formula:

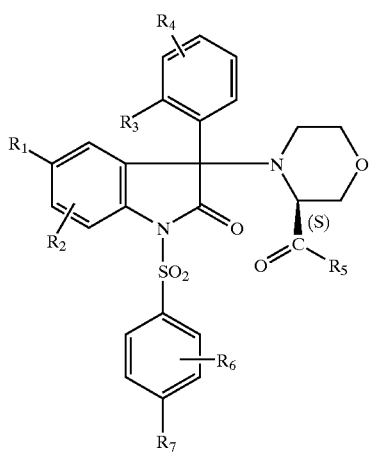

(I)

in which:
  $R_1$ represents a halogen atom; a $(C_1-C_4)$alkyl; a $(C_1-C_4)$ alkoxy; a trifluoromethyl radical; or a trifluoromethoxy radical;
  $R_2$ represents a hydrogen atom; a halogen atom; a $(C_1-C_4)$alkyl; a $(C_1-C_4)$alkoxy; or a trifluoromethyl radical;
  or else $R_2$ is in the 6-position of the indol-2-one ring and $R_1$ and $R_2$ together represent the bivalent trimethylene radical;
  $R_3$ represents a halogen atom; a hydroxyl; a $(C_1-C_2)$alkyl; a $(C_1-C_2)$alkoxy; or a trifluoromethoxy radical;
  $R_4$ represents a hydrogen atom; a halogen atom; a $(C_1-C_2)$alkyl; or a $(C_1-C_2)$alkoxy;
  or else $R_4$ is in the 3-position of the phenyl and $R_3$ and $R_4$ together represent the methylenedioxy radical;
  $R_5$ represents an ethylamino group; a dimethylamino group; an azetidin-1-yl radical; or a $(C_1-C_2)$alkoxy;
  $R_6$ represents a $(C_1-C_4)$alkoxy;
  $R_7$ represents a $(C_1-C_4)$alkoxy;
and their solvates and/or hydrates.

The term "halogen atom" is understood to mean a chlorine, bromine, fluorine or iodine atom.

The term "alkyl" or the term "alkoxy" are respectively understood to mean a linear or branched alkyl or alkoxy radical respectively.

The compounds of formula (I) comprise at least 2 asymmetric carbon atoms, the carbon atom being the $COR_5$ substituent in the (S) configuration. The optically pure isomers of the compounds of formula (I) and their mixtures in any proportion form part of the invention.

According to the present invention, preference is given to the compounds of formula (I) in which:
  $R_1$ represents a halogen atom; a $(C_1-C_4)$alkyl; a trifluoromethyl radical; or a trifluoromethoxy radical;
  $R_2$ represents a hydrogen atom; a halogen atom; a $(C_1-C_4)$alkyl; a $(C_1-C_4)$alkoxy; or a trifluoromethyl radical;
  or else $R_2$ is in the 6-position of the indol-2-one ring and $R_1$ and $R_2$ together represent the bivalent trimethylene radical;
  $R_3$ represents a halogen atom; a hydroxyl; or a $(C_1-C_2)$ alkoxy;
  $R_4$ represents a hydrogen atom; a halogen atom; a $(C_1-C_2)$alkyl; or a $(C_1-C_2)$alkoxy;
  or else $R_4$ is in the 3-position of the phenyl and $R_3$ and $R_4$ together represent the methylenedioxy radical;
  $R_5$ represents an ethylamino group; a dimethylamino group; an azetidin-1-yl radical; or a $(C_1-C_2)$ alkoxy;
  $R_6$ represents a $(C_1-C_4)$alkoxy;
  $R_7$ represents a $(C_1-C_4)$alkoxy;
and their solvates and/or hydrates.

According to the present invention, preference is given to the compounds of formula (I) in which $R_1$ represents a chlorine atom, a methyl radical or a trifluoromethoxy radical.

According to the present invention, preference is given to the compounds of formula (I) in which $R_2$ represents a hydrogen atom or is in the 6-position of the indol-2-one and represents a chlorine atom, a methyl radical, a methoxy radical or a trifluoromethyl radical.

According to the present invention, preference is given to the compounds of formula (I) in which $R_3$ represents a chlorine atom or a methoxy radical.

According to the present invention, preference is given to the compounds of formula (I) in which $R_4$ represents a hydrogen atom or is in the 3-position of the phenyl and represents a methoxy radical.

According to the present invention, preference is given to the compounds of formula (I) in which $R_5$ represents a dimethylamino group, an azetidin-1-yl radical or a methoxy radical.

According to the present invention, preference is given to the compounds of formula (I) in which $R_6$ is in the 2-position of the phenyl and represents a methoxy radical.

According to the present invention, preference is given to the compounds of formula (I) in which $R_7$ represents a methoxy radical.

Preference is more particularly given to the compounds of formula (I) in which:
  $R_1$ represents a chlorine atom or a methyl radical;
  $R_2$ represents a hydrogen atom or is in the 6-position of the indol-2-one and represents a chlorine atom or a methyl radical;
  $R_3$ represents a methoxy radical;
  $R_4$ represents a hydrogen atom;
  $R_5$ represents a dimethylamino group;
  $R_6$ is in the 2-position of the phenyl and represents a methoxy radical;
  $R_7$ represents a methoxy radical;
and their solvates and/or hydrates.

According to the present invention, preference is given to the compounds of formula (I) in the form of optically pure isomers, the carbon atom in the 3-position of the indol-2-one has either the (R) configuration or the (S) configuration.

Preference is most particularly given to the levorotatory isomer of the compounds of formula (I).

The following compounds:
  (3S)-4-[5-Chloro-1-[(2,4-dimethoxyphenyl)sulfonyl]-3-(2-methoxyphenyl)-2-oxo-2,3-dihydro-1H-indol-3-yl]-N,N-dimethylmorpholine-3-carboxamide, levorotatory isomer;

(3S)-4-[6-Chloro-1-[(2,4-dimethoxyphenyl)sulfonyl]-3-(2-methoxyphenyl)-5-methyl-2-oxo-2,3-dihydro-1H-indol-3-yl]-N,N-dimethylmorpholine-3-carboxamide, levorotatory isomer;

(3S)-4-[5-Chloro-1-[((2,4-dimethoxyphenyl)sulfonyl]-3-(2-methoxyphenyl)-6-methyl-2-oxo-2,3-dihydro-1H-indol-3-yl]-N,N-dimethylmorpholine-3-carboxamide, levorotatory isomer;

and their solvates and/or hydrates are more particularly preferred.

According to another of its aspects, the subject of the present invention is a process for the preparation of the compounds of formula (I), their solvates and/or their hydrates, characterized in that:

a compound of formula:

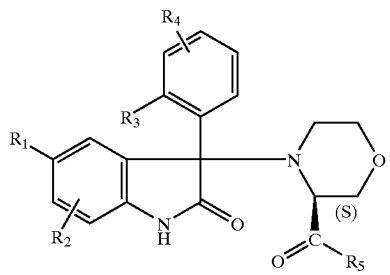

(II)

in which $R_1$, $R_2$, $R_3$, $R_4$ and $R_5$ are as defined for a compound of formula (I), is reacted, in the presence of a base, with a halide of formula:

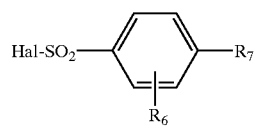

(III)

in which $R_6$ and $R_7$ are as defined for a compound of formula (I) and Hal represents a halogen atom.

The reaction is carried out in the presence of a strong base, such as a metal hydride, for example sodium hydride, or an alkali metal alkoxide, for example potassium tert-butoxide, in an anhydrous solvent, such as N,N-dimethylformamide or tetrahydrofuran, and at a temperature of between −70° C. and +60° C. The reaction is preferably carried out by using a compound of formula (III) in which Hal=Cl.

The compounds of formula (I) thus obtained can subsequently be separated from the reaction mixture and purified according to conventional methods, for example by crystallization or chromatography.

The compounds of formula (II) are prepared by the reaction of a 3-halo-1,3-dihydro-2H-indol-2-one compound of formula:

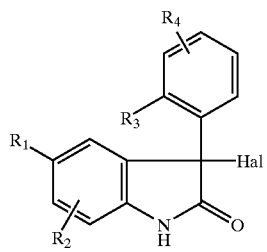

(IV)

in which $R_1$, $R_2$, $R_3$ and $R_4$ are as defined for a compound of formula (I) and Hal represents a halogen atom, preferably chlorine or bromine, with a compound of formula:

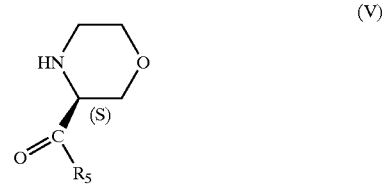

(V)

in which $R_5$ is as defined for a compound of formula (I).

The reaction is carried out in the presence of a base, such as diisopropylethylamine or triethylamine, in an inert solvent, such as dichloromethane or tetrahydrofuran or a mixture of these solvents, and at a temperature of between ambient temperature and the reflux temperature of the solvent.

The compounds of formula (III) are known or prepared by known methods, such as those disclosed in EP-0 469 984 B and WO 95/18105. For example, the compounds of formula (III) can be prepared by halogenation of the corresponding benzenesulfonic acids or of their salts, for example of their sodium or potassium salts. The reaction is carried out in the presence of a halogenating agent, such as phosphorus oxychloride, thionyl chloride, phosphorus trichloride, phosphorus tribromide or phosphorus pentachloride, without a solvent or in an inert solvent, such as a halogenated hydrocarbon or N,N-dimethylformamide, and at a temperature of between −10° C. and 200° C.

2,4-Dimethoxybenzenesulfonyl chloride is prepared according to J. Am. Chem. Soc., 1952, 74, 2008. 3,4-Dimethoxybenzenesulfonyl chloride is commercially available or prepared according to J. Med. Chem., 1977, 20 (10), 1235–1239.

The compounds of formula (IV) are known and are prepared according to known methods, such as those disclosed in WO 95/18105.

For example, a compound of formula:

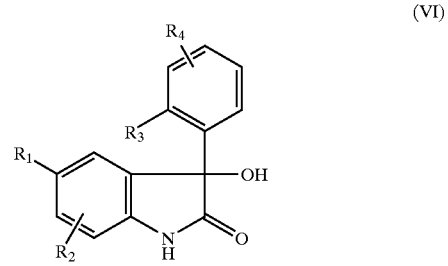

(VI)

in which $R_1$, $R_2$, $R_3$ and $R_4$ are as defined for a compound of formula (I), is converted into a compound of formula (IV) in which Hal=Cl by the action of thionyl chloride in the presence of a base, such as pyridine, in an inert solvent, such as dichloromethane, and at a temperature between 0° C. and ambient temperature.

According to another example of the preparation of the compounds of formula (IV), a compound of formula:

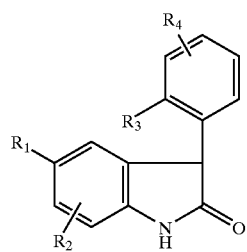

(VII)

in which $R_1$, $R_2$, $R_3$ and $R_4$ are as defined for a compound of formula (I), is converted into a compound of formula (IV) by means of a halogenating agent, such as bromine, according to the process described in Farm. Zh. (Kiev), 1976, 5, 30–33.

The compounds of formula (VI) are known and are prepared according to known methods, such as those disclosed in WO 95/18105.

For example, a compound of formula (VI) is prepared by reaction of a 1H-indole-2,3-dione derivative of formula:

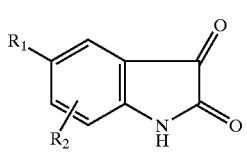

(VIII)

in which $R_1$ and $R_2$ are as defined for a compound of formula (I), with an organomagnesium derivative of formula:

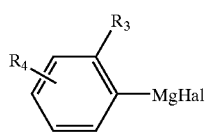

(IX)

in which $R_3$ and $R_4$ are as defined for a compound of formula (I) and Hal represents a halogen atom, preferably bromine or iodine, in an inert solvent, such as tetrahydrofuran or diethyl ether, and at a temperature of between 0° C. and the reflux temperature of the solvent.

A compound of formula (VI) in which $R_3$ is as defined for a compound of formula (I) and $R_4$, which is other than hydrogen, is in the 3- or 6-position of the phenyl can also be prepared by the reaction of a compound of formula:

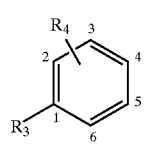

(XVI)

in which $R_3$ is as defined for a compound of formula (I) and $R_4$ is in the 2- or 5-position of the phenyl, with a lithium derivative, such as n-butyllithium, and then the lithiated intermediate thus obtained is reacted with a compound of formula (VIII). The reaction is carried out in a solvent, such as diethyl ether, tetrahydrofuran, hexane or a mixture of these solvents, at a temperature of between −70° C. and ambient temperature.

The 1H-indole-2,3-dione derivatives (VIII) are commercially available or prepared according to the methods described in Tetrahedron Letters, 1998, 39, 7679–7682; Tetrahedron Letters, 1994, 35, 7303–7306; J. Org. Chem., 1977, 42 (8), 1344–1348; J. Org. Chem., 1952, 17, 149–156; J. Am. Chem. Soc., 1946, 68, 2697–2703; Organic Syntheses, 1925, V, 71–74 and Advances in Heterocyclic Chemistry, A. R. Katritzky and A. J. Boulton, Academic Press, New York, 1975, 18, 2–58.

The organomagnesium derivatives (IX) are prepared according to conventional methods well known to a person skilled in the art.

A compound of formula (VI) can also be prepared by air oxidation of a compound of formula (VII) in the presence of a base, such as sodium hydride, and in the presence of dimethyl disulfide.

Specifically, the compounds of formula (VI) in which $R_3=(C_1-C_2)$alkoxy and $R_4$=H or else $R_3=R_4=(C_1-C_2)$alkoxy with $R_4$ in the 3- or 6-position of the phenyl, $R_2$ is other than a halogen atom and $R_1$ is as defined for a compound of formula (I) can be prepared by following the process described in SCHEME 1.

SCHEME 1

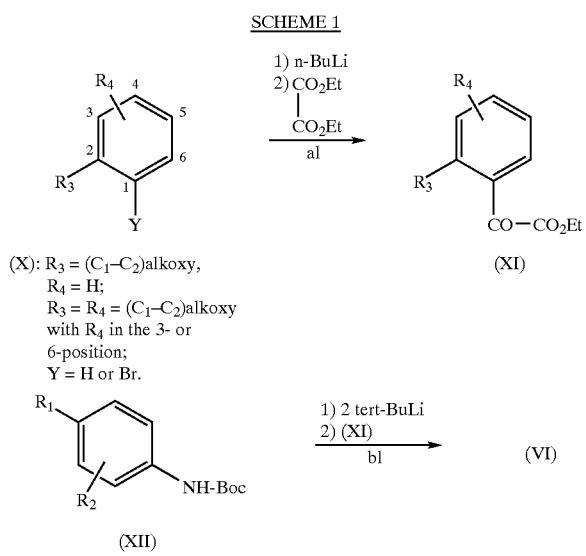

(X): $R_3$ = $(C_1-C_2)$alkoxy, $R_4$ = H; $R_3$ = $R_4$ = $(C_1-C_2)$alkoxy with $R_4$ in the 3- or 6-position; Y = H or Br.

In stage a1 of SCHEME 1, a compound of formula (X) is first of all reacted with a lithium derivative, such as n-butyllithium, in the absence or in the presence of a base, such as N,N,N',N'-tetramethylenediamine, and then the lithiated intermediate thus obtained is reacted with diethyl oxalate to give the compound of formula (XI). The reaction is carried out in an inert solvent, such as diethyl ether or tetrahydrofuran, and at a temperature of between −70° C. and ambient temperature.

In stage b1, a compound of formula (XII) is first of all reacted with two equivalents of a lithium derivative, such as tert-butyllithium, and then the lithiated intermediate obtained is reacted with the compound of formula (XI) to give the expected compound of formula (VI). The reaction is carried out in an inert solvent, such as diethyl ether or tetrahydrofuran, and at a temperature of between −70° C. and ambient temperature.

The compounds of formula (X) are commercially available or are synthesized in a conventional way.

The compounds of formula (XII) are prepared by reaction of the corresponding aniline derivatives with di-tert-butyl dicarbonate according to conventional methods.

The compounds of formula (VII) are known and are prepared according to known methods, such as those disclosed in WO 95/18105 or in J. Org. Chem., 1968, 33, 1640–1643.

The compounds of formula (V) are known or are prepared according to known methods. Thus, for example, the compounds of formula (V) in which $R_5$ represents an ethylamino or dimethylamino group or an azetidin-1-yl radical are prepared according to SCHEME 2 below, in which Pr represents an N-protecting group, in particular benzyl or tert-butoxycarbonyl, and R represents a ($C_1$–$C_2$)alkyl.

SCHEME 2

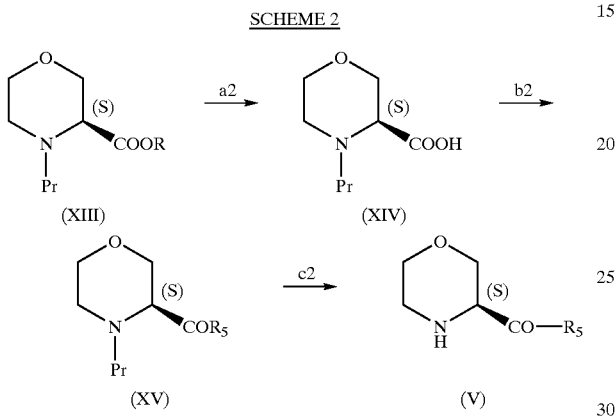

In stage a2 of SCHEME 1, an ester of formula (XIII) is esterified according to conventional methods, to obtain an acid of formula (XIV).

The acid (XIV) is reacted in stage b2 with ethylamine, dimethylamine or azetidine according to conventional peptide coupling methods to give the compound (XV), which is deprotected in stage c2, according to known methods, to give an expected compound of formula (V).

A compound of formula (XIV) may also be prepared by protecting, according to conventional methods, (3S)-morpholine-3-carboxylic acid; the latter is prepared according to the process described in Bull. Chem. Soc. Jpn. 1987, 60 (8), 2963–2965.

The compounds of formula (V) in which $R_5$ represents a ($C_1$–$C_2$)alkoxy are obtained by various known methods, in particular by deprotection of the compounds of formula (XIII).

The chiral compounds of formula (XIII) are prepared from (S)-serine according to the process described in J. Chem. Soc. Perkin Trans I, 1985, 2577–2580.

When it is desired to prepare an optically pure compound of formula (I), an optically pure compound of formula (II) is preferably reacted with a compound of formula (III) according to the process of the invention.

The optically pure compounds of formula (II) are prepared by reaction of the racemic compound of formula (IV) with an optically pure compound of formula (V), followed by separation of the mixture of diastereoisomers according to conventional methods, for example by crystallization or chromatography.

Alternatively, the mixture of diastereoisomers of the compound of formula (II) can be reacted with the compound of formula (III) and the mixture of diastereoisomers of the compound of formula (I) thus obtained can be separated.

During any one of the stages for the preparation of the compounds of formula (I) or of the intermediate compounds of formula (II), (IV), (V) or (VI), it may be necessary and/or desirable to protect the reactive or sensitive functional groups, such as amine, hydroxyl or carboxyl groups, present on any one of the molecules concerned. This protection can be achieved by using conventional protecting groups, such as those described in Protective Groups in Organic Chemistry, J. F. W. McOmie, published by Plenum Press, 1973, in Protective Groups in Organic Synthesis, T. W. Greene and P. G. M. Wutts, published by John Wiley and Sons, 1991 or in Protecting Groups, Kocienski P. J., 1994, Georg Thieme Verlag. The protecting groups can be removed at an appropriate subsequent stage using methods known to a person skilled in the art which do not affect the remainder of the molecule concerned.

The N-protecting groups optionally used are conventional N-protecting groups well known to a person skilled in the art, such as, for example, the tert-butyoxycarbonyl, fluorenylmethoxycarbonyl, benzyl, benzhydrylidene or benzyloxycarbonyl group.

The compounds of formula (II) are novel and form part of the invention.

Thus, according to another of its aspects, a subject of the invention is compounds of formula:

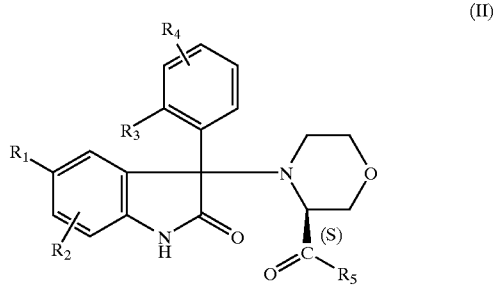

in which:

$R_1$ represents a halogen atom; a ($C_1$–$C_4$)alkyl; a ($C_1$–$C_4$) alkoxy; a trifluoromethyl radical; or a trifluoromethoxy radical;

$R_2$ represents a hydrogen atom; a halogen atom; a ($C_1$–$C_4$)alkyl; a ($C_1$–$C_4$)alkoxy; or a trifluoromethyl radical;

or else $R_2$ is in the 6-position of the indol-2-one ring and $R_1$ and $R_2$ together represent the bivalent trimethylene radical;

$R_3$ represents a halogen atom; a hydroxyl; a ($C_1$–$C_2$)alkyl; a ($C_1$–$C_2$)alkoxy; or a trifluoromethoxy radical;

$R_4$ represents a hydrogen atom; a halogen atom; a ($C_1$–$C_2$)alkyl; or a ($C_1$–$C_2$)alkoxy;

or else $R_4$ is in the 3-position of the phenyl and $R_3$ and $R_4$ together represent the methylenedioxy radical;

$R_5$ represents an ethylamino group; a dimethylamino group; an azetidin-1-yl radical; or a ($C_1$–$C_2$)alkoxy;

and their salts with inorganic or organic acids, in the form of optically pure isomers or in the form of a mixture of diastereoisomers.

The salts of the compounds of formula (II) comprise those with inorganic or organic acids which make possible suitable separation or crystallization of the compounds of formula (II), such as the hydrochloride, hydrobromide, oxalate, maleate, succinate, fumarate, citrate or acetate.

The compounds of above formula (I) also comprise those in which one or more hydrogen or carbon atoms have been replaced by their radioactive isotope, for example tritium or carbon-14. Such labeled compounds are of use in research, metabolism or pharmacokinetic studies or in biochemical assays as receptor ligand.

The compounds according to the invention have formed the subject of biochemical studies.

The affinity of the compounds of formula (I) according to the invention for arginine-vasopressin $V_{1b}$ receptors was determined in vitro by using the method described by Y. De Keyser et al., FEBS Letters, 1994, 356, 215–220. This method consists in studying in vitro the displacement of tritiated arginine-vasopressin ($[^3H]$-AVP) at the $V_{1b}$ receptors present on adenohypophysal membrane or cell preparations carrying rat or human $V_{1b}$ receptors. The 50% inhibitory concentrations ($IC_{50}$) for the attachment of tritiated arginine-vasopressin of the compounds according to the invention are low and vary from $10^{-6}$ to $10^{-9}M$, more particularly $10^{-8}M$.

The affinity of the compounds of formula (I) according to the invention for arginine-vasopressin $V_{1a}$ receptors was determined in vitro using the method described by M. Thibonnier et al., J. Biol. Chem., 1994, 269, 3304–3310. This method consists in studying in vitro the displacement of tritiated arginine-vasopressin ($[^3H]$-AVP) at the $V_{1a}$ receptors present on membrane or cell preparations carrying rat or human $V_{1a}$ receptors. Some of the compounds of formula (I) also exhibit an affinity for arginine-vasopressin $V_{1a}$ receptors, with $IC_{50}$ values which vary from $10^{-6}$ to $10^{-9}M$, more particularly $10^{-7}M$.

The affinity of the compounds of formula (I) according to the invention for vasopressin $V_2$ receptors has also been studied (method described by M. Birnbaumer et al., Nature (Lond.), 1992, 357, 333–335). The compounds studied have little or no affinity for the $V_2$ receptors.

The compounds of the present invention are in particular active ingredients of pharmaceutical compositions, the toxicity of which is compatible with their use as medicaments.

According to another of its aspects, the present invention relates to the use of the compounds of formula (I), of their solvates and/or of their hydrates which are pharmaceutically acceptable for the preparation of medicaments intended for the treatment of any pathology where arginine-vasopressin and/or its $V_{1b}$ receptors or both its $V_{1b}$ receptors and its $V_{1a}$ receptors are implicated.

According to another of its aspects, the present invention relates to the use of the compounds of formula (I), of their solvates and/or of their hydrates which are pharmaceutically acceptable in the preparation of medicaments intended for the treatment of pathologies of the cardiovascular system, of the central nervous system, of the renal system or of the gastric system and of small cell lung cancers, obesity, type-II diabetes, insulin resistance, hypertrigyeridemia, atherosclerosis, Cushing's syndrome or any pathology resulting from stress and chronic stress conditions.

Thus, the compounds according to the invention may be used, in man or in animals, in the treatment or prevention of various vasopressin-dependent conditions, such as cardiovascular conditions, for example hypertension, pulmonary hypertension, cardiac insufficiency, myocardial infarction or coronary vasospasm, in particular in smokers, Raynaud's syndrome, unstable angina and PTCA (percutaneous transluminal coronary angioplasty), cardiac ischemia or hemostasis disturbances; conditions of the central nervous system, such as migraine, cerebral vasospasm, cerebral hemorrhage, cerebral edema, depression, anxiety, stress, obsessive-compulsive disorder, panic attacks, psychotic states or memory disorders, for example; conditions of the renal system, such as renal vasospasm, necrosis of the renal cortex; nephrogenic diabetes insipidus; conditions of the gastric system, such as gastric vasospasm, cirrhosis of the liver, ulcers or the pathology of vomiting, for example nausea, including nausea due to chemotherapy or travel sickness; or diabetic nephropathy. The compounds according to the invention can also be used in the treatment of disorders of sexual behavior; in women, the compounds according to the invention can be used to treat dysmenorrhoea or premature labor. The compounds according to the invention can also be used in the treatment of small cell lung cancers; hyponatremic encephalopathy; pulmonary syndrome, Ménière's disease; glaucoma, cataracts; obesity; type-II diabetes; atherosclerosis; Cushing's syndrome; insulin resistance, or hypertriglyceridemia, or in post-operative treatments, in particular after abdominal surgery.

The compounds according to the invention can also be used in the treatment or prevention of any pathology resulting from stress, such as fatigue and its syndromes, ACTH-dependent disorders, cardiac disorders, pain, modifications in gastric emptying, in fecal excretion (colitis, irritable bowel syndrome or Crohn's disease) or in acid secretion, hyperglycemia, immunosuppression, inflammatory processes (rheumatoid arthritis and osteoarthritis), multiple infections, cancers, asthma, psoriasis, allergies and various neuropsychiatric disorders, such as anorexia nervosa, bulimia, mood disorders, depression, anxiety, sleep disorders, panic states, phobias, obsession, disorders of pain perception (fibromyalgia), neurodegenerative diseases (Alzheimer's disease, Parkinson's disease or Huntington's disease), substance dependence, hemorrhagic stress, muscle spasms or hypoglycemia. The compounds according to the invention can also be used in the treatment or prevention of chronic stress conditions, such as immunodepression, fertility disorders or dysfunctionings of the hypothalamopituitaryadrenal axis.

The compounds according to the invention can also be used as psychostimulants, resulting in an increase in alertness or emotional reactivity to the surroundings and making adaptation easier.

The compounds of above formula (I), their solvates and/or their hydrates which are pharmaceutically acceptable can be used at daily doses of 0.01 to 100 mg per kilo of body weight of the mammal to be treated, preferably at daily doses of 0.1 to 50 mg/kg. In man, the dose can preferably vary from 0.1 to 4000 mg per day, more particularly from 0.5 to 1000 mg, depending upon the age of the subject to be treated or the type of treatment; prophylactic or curative.

For their use as medicaments, the compounds of formula (I) are generally administered in dosage units. Said dosage units are preferably formulated in pharmaceutical compositions in which the active ingredient is mixed with one or more pharmaceutical excipients.

Thus, according to another of its aspects, the present invention relates to pharmaceutical compositions including, as active ingredient, a compound of formula (I), one of its solvates and/or one of its hydrates which are pharmaceutically acceptable.

In the pharmaceutical compositions of the present invention for administration by the oral, sublingual, inhaled, subcutaneous, intramuscular, intravenous, transdermal, local or rectal route, the active ingredients can be administered in single-dose administration forms, as a mixture with conventional pharmaceutical vehicles, to animals and human beings. The appropriate single-dose administration forms comprise forms by the oral route, such as tablets, gelatin capsules, powders, granules and oral solutions or suspensions, sublingual and buccal administration forms, aerosols, topical administration forms, implants, subcutaneous, intramuscular, intravenous, intranasal or intraocular administration forms and rectal administration forms.

When a solid composition is prepared in the form of tablets or gelatin capsules, a mixture of pharmaceutical excipients is added to the micronized or nonmicronized active ingredient, which mixture can be composed of diluents, such as, for example, lactose, microcrystalline cellulose, starch or dicalcium phosphate, of binders, such as, for example, polyvinylpyrrolidone or hydroxypropylmethylcellulose, of disintegrating agents, such as crosslinked polyvinylpyrrolidone or crosslinked carboxymethylcellulose, of flow agents, such as silica or talc, or of lubricants, such as magnesium stearate, stearic acid, glyceryl tribehenate or sodium stearylfumarate.

Wetting agents or surfactants, such as sodium lauryl sulfate, polysorbate 80 or poloxamer 188, can be added to the formulation.

The tablets can be prepared by various techniques: direct tableting, dry granulation, wet granulation or hot-melt.

The tablets can be bare or sugar-coated (with sucrose, for example) or coated with various polymers or other appropriate materials.

The tablets can have a flash, delayed or sustained release by preparing polymeric matrices or by using specific polymers when forming the thin film.

The gelatin capsules may be soft or hard and may or may not be coated with a thin film, so as to have a flash, sustained or delayed activity (for example via an enteric form).

They can comprise not only a solid formulation formulated as above for tablets but also liquids or semi-solids.

A preparation in the form of a syrup or elixir can comprise the active ingredient in conjunction with a sweetener, preferably a calorie-free sweetener, methylparaben and propylparaben, as antiseptic, a flavoring agent and an appropriate colorant.

The water-dispersible powders or granules can comprise the active ingredient as a mixture with dispersing agents, wetting agents or suspending agents, such as polyvinylpyrrolidone, as well as with sweeteners or flavor enhancers.

For rectal administration, recourse is had to suppositories which are prepared with binders which melt at the rectal temperature, for example cocoa butter or polyethylene glycols.

For parenteral, intranasal or intraocular administration, use is made of aqueous suspensions, isotonic saline solutions or sterile and injectable solutions which comprise pharmacologically compatible dispersing agents and/or solubilizing agents, for example propylene glycol.

Thus, to prepare an aqueous solution which can be injected by the intravenous route, use may be made of a cosolvent, such as, for example, an alcohol, such as ethanol, or a glycol, such as polyethylene glycol or propylene glycol, and of a hydrophilic surfactant, such as polysorbate 80 or poloxamer 188. To prepare an oily solution which can be injected by the intramuscular route, the active ingredient can be dissolved with a triglyceride or a glyceryl ester.

For local administration, use may be made of creams, ointments, gels, eyewashes or sprays.

For transdermal administration, use may be made of patches in multilaminar or reservoir form, in which the active ingredient can be in alcoholic solution, or sprays.

For administration by inhalation, use is made of an aerosol comprising, for example, sorbitan trioleate or oleic acid and trichlorofluoromethane, dichlorofluoromethane, dichlorotetrafluoroethane, freon substitutes or any other biologically compatible propellant gas; use may also be made of a system comprising the active ingredient, alone or in combination with an excipient, in powder form.

The active ingredient can also be presented in the form of a complex with a cyclodextrin, for example α-, β- or γ-cyclodextrin or 2-hydroxypropyl-β-cyclodextrin.

The active ingredient can also be formulated in the form of microcapsules or microspheres, optionally with one or more vehicles or additives.

Use may be made of implants among the sustained-release forms of use in the case of chronic treatments. These implants can be prepared in the form of an oily suspension or in the form of a suspension of microspheres in an isotonic medium.

The active ingredient of formula (I) is present in each dosage unit in the amounts suited to the daily doses envisaged. In general, each dosage unit is suitably adjusted according to the dosage and the type of administration provided, for example tablets, gelatin capsules and the like, sachets, ampules, syrups and the like, or drops, so that such a dosage unit comprises from 0.1 to 1000 mg of active ingredient, preferably from 0.5 to 250 mg, which has to be administered one to four times daily.

Although these dosages are examples of average situations, there may be specific cases where higher or lower dosages are appropriate; such dosages also form part of the invention. According to the usual practice, the dosage appropriate to each patient is determined by the physician according to the method of administration and the age, the weight and the response of said patient.

The compositions of the present invention can comprise, in addition to the compounds of formula (I), their solvates and/or their hydrates which are pharmaceutically acceptable, other active ingredients which can be of use in the treatment of the disorders or diseases indicated above.

Thus, another subject of the present invention is pharmaceutical compositions comprising several active ingredients in combination, one of which is a compound according to the invention.

Thus, according to the present invention, pharmaceutical compositions can be prepared which comprise a compound according to the invention in combination with a compound which has an effect on the CRF receptors.

The compounds according to the invention can also be used for the preparation of compounds for veterinary use.

The following PREPARATIONS and EXAMPLES illustrate the invention without, however, limiting it.

Use is made, in the Preparations and in the Examples, of the following abbreviations:

ether: diethyl ether
iso ether: diisopropyl ether
DMF: N,N-dimethylformamide
THF: tetrahydrofuran
DCM: dichloromethane
AcOEt: ethyl acetate
DIPEA: diisopropylethylamine
TFA: trifluoroacetic acid
Boc: tert-butoxycarbonyl
Cbz: benzyloxycarbonyl
BOP: benzotriazol-1-yloxytris(dimethylamino) phosphonium hexafluorophosphate
PyBOP: benzotriazol-1-yloxytripyrrolidino-phosphonium hexafluorophosphate
DCC: 1,3-dicyclohexylcarbodiimide
HOBT: 1-hydroxybenzotriazole hydrate M.p.: melting point AT: ambient temperature B.p.: boiling point HPLC: high performance liquid chromatography.

The proton magnetic resonance spectra ($^1$H NMR) are recorded at 200 MHz in $d_6$-DMSO using the $d_6$-DMSO peak as reference. The chemical shifts δ are expressed in parts per million (ppm). The signals observed are expressed thus: s: singlet; bs: broad singlet; d: doublet; dd: double doublet; t: triplet; q: quartet; up: unresolved peak; mt: multiplet.

The mass spectra indicate the value MH$^+$.

Preparations

Preparations of the compounds of formula (IV).

Preparation 1.1

3,5-Dichloro-3-(2-methoxyphenyl)-1,3-dihydro-2H-indole-2-one.

(IV): $R_1$=Cl; $R_2$=H; $R_3$=OCH$_3$; $R_4$=H; Hal=Cl.

A) 5-Chloro-3-hydroxy-3-(2-methoxyphenyl)-1,3-dihydro-2H-indol-2-one.

This compound is prepared according to the procedure disclosed in WO 95/18105. A solution of 2-methoxyphenylmagnesium bromide is prepared from 16 g of magnesium in 35 ml of ether and from a solution of 124 g of 1-bromo-2-methoxybenzene in 175 ml of ether. This solution is added dropwise under an argon atmosphere to a mixture, cooled beforehand in an ice bath, of 30 g of 5-chloro-1H-indole-2,3-dione in 250 ml of THF and then the mixture is left stirring while allowing the temperature to rise to AT. After stirring for 1 hour at AT, the reaction mixture is slowly poured onto a saturated NH$_4$Cl solution and the THF is evaporated under vacuum. The precipitate formed is filtered off and is washed with iso ether. 42 g of the expected product are obtained, which product is used as is in the following stage.

B) 3,5-Dichloro-3-(2-methoxyphenyl)-1,3-dihydro-2H-indol-2-indol-2-one.

This compound is prepared according to the procedure disclosed in WO 95/18105. A mixture of 12.71 g of the compound obtained in the preceding stage in 105 ml of DCM is cooled to 0° C., 5.3 ml of pyridine are added and then 4.9 ml of thionyl chloride are added. After stirring for 30 minutes, water is added to the reaction mixture and the DCM is evaporated under vacuum. The precipitate formed is filtered off, washed three times with water and then three times with iso ether, and dried. 13.66 g of the expected product are obtained, which product is used as is.

Preparation 1.2

3,6-Dichloro-3-(2-methoxyphenyl)-5-methyl-1,3-dihydro-2H-indol-2-one.

(IV): $R_1$=CH$_3$; $R_2$=6-Cl; $R_3$=OCH$_3$; $R_4$=H; Hal=Cl.

A) 6-Chloro-5-methyl-3-methylthio-1,3-dihydro-2H-indol-2-one and 4-chloro-5-methyl-3-methylthio-1,3-dihydro-2H-indol-2-one.

8.5 ml of chlorine are introduced into 320 ml of DCM, cooled to −70° C., then a solution of 24 ml of ethyl methylthioacetate in 60 ml of DCM is added over 20 minutes at −70° C. and the mixture is left stirring for 15 minutes at −70° C. A solution of 52.64 g of 3-chloro-4-methylaniline in 100 ml of DCM is subsequently added at −70° C. over 30 minutes and the mixture is left stirring for 1 hour 45 minutes at −70° C. Finally, 41.3 ml of triethylamine are added at −70° C. and the mixture is left stirring for 1 hour while allowing the temperature to rise to AT. The reaction mixture is washed twice with 250 ml of water, the organic phase is dried over MgSO$_4$ and the solvent is evaporated under vacuum. The residue is taken up in a mixture of 600 ml of ether and 130 ml of 2N HCl and the mixture is left stirring for 72 hours at AT. An insoluble material is filtered off, the filtrate is separated by settling, the organic phase is washed twice with water and dried over MgSO$_4$, and the solvent is evaporated under vacuum. The residue is chromatographed on silica gel, elution being carried out with DCM and then with a DCM/AcOEt (85/15; v/v) mixture. The mixture obtained is rechromatographed on silica gel, elution being carried out with DCM and then with a DCM/AcOEt (95/5; v/v) mixture. The two isomers are separated:

the less polar isomer, which is 6-chloro-5-methyl-3-methylthio-1,37dihydro-2H-indol-2-one, and 1.16 g are obtained, the more polar isomer, which is 4-chloro-5-methyl-3-methylthio-1,3-dihydro-2H-indol-2-one, and 0.72 9 is obtained.

B) 6-Chloro-5-methyl-1H-indole-2,3-dione.

A mixture of 1.16 g of 6-chloro-5-methyl-3-methylthio-1,3-dihydro-2H-indol-2-one, obtained in the preceding stage, and 0.681 g of N-chlorosuccinimide in 100 ml of carbon tetrachloride is heated at reflux for 1 hour. The reaction mixture is concentrated under vacuum and the residue is taken up in a mixture of 80 ml of THF and 20 ml of water and then heated at reflux for 16 hours. The THF is evaporated under vacuum, the remaining aqueous phase is extracted with AcOEt, the organic phase is washed with water and with a saturated NaCl solution and dried over Na$_2$SO$_4$, and the solvent is evaporated under vacuum. The residue is chromatographed on silica gel, elution being carried out with DCM and then with the gradient of the DCM/AcOEt mixture up to (85/15; v/v). 0.793 g of the expected product is obtained, M.p.=264° C.

C) 6-Chloro-3-hydroxy-3-(2-methoxyphenyl)-5-methyl-1,3-dihydro-2H-indol-2-one.

A solution of 2-methoxyphenylmagnesium bromide is prepared from 0.687 g of magnesium in 1.5 ml of ether and from a solution of 5.35 g of 1-bromo-2-methoxybenzene in 7.55 ml of ether. This solution is added dropwise, under an argon atmosphere, to a mixture, cooled beforehand in an ice bath, of 1.4 g of the compound obtained in the preceding stage in 14 ml of THF and then the mixture is left stirring while allowing the temperature to rise to AT. After stirring for 1 hour at AT, the reaction mixture is slowly poured onto a saturated NH$_4$Cl solution, the THF is evaporated under vacuum, extraction is carried out with AcOEt, the organic phase is washed with water and with a saturated NaCl solution and dried over Na$_2$SO$_4$, and the AcOEt is evaporated under vacuum. The residue is chromatographed on silica gel, elution being carried out with DCM and then with a DCM/MeOH (98/2; v/v) mixture. 1.6 g of the expected product are obtained after crystallization from a THF/MeOH mixture, M.p.=266° C.

D) 3,6-Dichloro-3-(2-methoxyphenyl)-5-methyl-1,3-dihydro-2H-indol-2-one.

A suspension of 1.7 g of the compound obtained in the preceding stage in 10 ml of DCM is cooled in an ice bath, 1.4 ml of pyridine and then 1.4 ml of thionyl chloride are added and the mixture is left stirring at AT. Water is added to the reaction mixture; after separation by settling, the organic phase is washed-with water to pH=7, dried over Na$_2$SO$_4$ and the solvent is evaporated under vacuum. 1.09 g of the expected product are obtained after crystallization from a DCM/iso ether mixture.

Preparation 1.3

3,5-Dichloro-3-(2-methoxyphenyl)-6-methyl-1,3-dihydro-2H-indol-2-one.

(IV): $R_1$=Cl; $R_2$=6-$CH_3$; $R_3$=$OCH_3$; $R_4$=H; Hal=Cl.

A) Ethyl 2-(2-methoxyphenyl)-2-oxoacetate.

A solution of 27 g of 1-bromo-2-methoxybenzene in 270 ml of ether is cooled to −70° C. under an argon-atmosphere, 90 ml of a 1.6M solution of n-butyllithium in pentane are added dropwise and then the mixture is left stirring for 45 minutes. 78 ml of diethyl oxalate are rapidly added and the mixture is left stirring while allowing the temperature to rise to AT. After stirring for 1 hour at AT, a saturated $NH_4Cl$ solution is added to the reaction mixture, separation by settling is carried out, the aqueous phase is extracted with ether, the combined organic phases are washed with water and with a saturated NaCl solution and dried over $Na_2SO_4$, and the solvents are evaporated under vacuum. The excess diethyl oxalate is removed by vacuum distillation (B.p.=87° C. under 2000 Pa). The resulting product is chromatographed on silica gel, elution being carried out with a DCM/hexane (50/50; v/v) mixture and then with DCM. The product obtained is purified by vacuum distillation. 13 g of the expected product are obtained, B.p.=110° C. under 3 Pa.

B) 5-Chloro-3-hydroxy-3-(2-methoxyphenyl)-6-methyl-1,3-dihydro-2H-indol-2-one.

a) tert-Butyl 4-chloro-3-methylphenylcarbamate.

A mixture of 10 g of 4-chloro-3-methylaniline and 15.26 g of di-tert-butyl dicarbonate in 50 ml of dioxane is left stirring for 24 hours at AT. The reaction mixture is concentrated under vacuum and the residue is chromatographed on silica gel, elution being carried out with the gradient of the DCM/hexane mixture from (50/50; v/v) to (70/30; v/v). 5.6 g of the expected product are obtained, which product is used as is.

b) A solution of 5 g of tert-butyl 4-chloro-3-methylphenylcarbamate in 45 ml of ether is cooled to −70° C. under an argon atmosphere, 30 ml of a 1.5M solution of tert-butyllithium in pentane are added dropwise, and the mixture is left stirring for 1 hour while raising the temperature to −10° C. and left stirring at −10° C. for 1 hour 45 minutes. The reaction mixture is cooled to −70° C., a solution of 5 g of the compound obtained in stage A in 25 ml of THF is added dropwise, and the mixture is left stirring for 1 hour while allowing the temperature to rise to −30° C. and then overnight while allowing the temperature to rise to AT. A saturated $NH_4Cl$ solution is added to the reaction mixture, the THF is evaporated, the resulting aqueous phase is extracted three times with AcOEt, the organic phase is washed with water and with a saturated NaCl solution and dried over $Na_2SO_4$, the solvent is partially evaporated and the crystalline product is filtered off. 2.6 g of the expected product are obtained, M.p.=254–256° C.

C) 3,5-Dichloro-3-(2-methoxyphenyl)-6-methyl-1,3-dihydro-2H-indol-2-one.

A mixture of 1.25 g of the compound obtained in stage B in 20 ml of DCM is cooled to 0° C., 0.5 ml of pyridine is added and then 0.47 ml of thionyl chloride is added, and the mixture is left stirring for 1 hour after having allowed the temperature to rise to AT.

Water and DCM are added to the reaction mixture, after separating by settling the organic phase is washed four times with water and dried over $Na_2SO_4$, and the solvent is evaporated under vacuum. 1.4 g of the expected product are obtained.

Preparation of the compounds of formula (V).

Preparation 2.1

(3S)-N,N-Dimethylmorpholine-3-carboxamide.

(V): $R_5$=—$N(CH_3)_2$.

A) (S)-N-Benzylserine.

28.5 ml of benzaldehyde are added dropwise to a solution of 30 g of (S)-serine in 150 ml of a 2M aqueous NaOH solution and the mixture is left stirring for 2 hours at AT. The reaction mixture is cooled to 4° C., 3 g of sodium borohydride are added in portions and the mixture is left stirring for 1 hour at 4° C. and then for 1 hour at AT. The reaction mixture is washed with ether, the aqueous phase is acidified to pH=6.5 by addition of a 10N HCl solution and the precipitate formed is filtered off. 20 g of the expected product are obtained after crystallization from water.

B) (3S)-4-benzyl-5-oxomorpholine-3-carboxylic acid.

A mixture of 20 g of the compound obtained in the preceding stage in 100 ml of water is cooled to 4° C., 5 g of NaOH.pellets are added and then 10 ml of chloroacetyl chloride are added dropwise and over 30 minutes. 30 ml of an aqueous 30% (weight/weight) NaOH solution are then added and the reaction mixture is heated at 30° C. for 2 hours. The reaction mixture is cooled to 4° C., acidified to pH=1 by addition of a 10N HCl solution and the precipitate formed is filtered off. 9 9 of the expected product are obtained.

C) Ethyl ester of (3S)-4-benzyl-5-oxomorpholine-3-carboxylic acid.

This compound is prepared using the method described by B. Neises and W. Steglich in Angew. Chem. Int. Ed. Engl., 1978, 17 (7), 522–524.

A mixture of 8 g of the compound obtained in the preceding stage in 40 ml of DCM and 2 ml of DMF is cooled to 4° C., 10 ml of EtOH, 1 g of 4-dimethylaminopyridine and 15 g of 1,3-dicyclohexylcarbodiimide are successively added, and then the reaction mixture is left stirring for 18 hours at AT. The insoluble material is filtered off and the filtrate is concentrated under vacuum. The residue is taken up in DCM and the insoluble material is again filtered off. The resulting organic phase is washed with an aqueous 5% $KHSO_4$ solution, with an aqueous 5% $NaHCO_3$ solution, dried over $Na_2SO_4$ and the solvent is evaporated under vacuum. The residue is chromatographed on silica gel, elution being carried out with a DCM/AcOEt (95/5; v/v) mixture. 8 g of the expected product are obtained.

D) Ethyl ester of (3S)-4-benzylmorpholine-3-carboxylic acid.

A solution of 7.8 g of the compound obtained in the preceding stage in 80 ml of anhydrous THF is cooled to 4° C. under a nitrogen atmosphere, 22 ml of a 2M solution of borane-dimethyl sulfide complex in THF are added and the reaction mixture is left stirring while allowing the temperature to rise to AT. After stirring for 3 hours at AT, water is added until the gaseous emission ceases. The THF is evaporated under vacuum, the resulting aqueous phase is alkalinized to pH=10 by addition of NaOH pellets, extracted with ether, the organic phase is dried over $MgSO_4$ and the solvent is evaporated under vacuum. The residue is chromatographed on silica gel, elution being carried out with a DCM/AcOEt (99/1; v/v) mixture. 4.7 g of the expected product are obtained.

E) (3S)-4-benzylmorpholine-3-carboxylic acid.

7 ml of an aqueous 50% NaOH solution are added at AT to a solution of 4.5 g of the compound obtained in the preceding stage in 20 ml of EtOH and the mixture is left stirring for 3 hours at AT. The reaction mixture is acidified to pH=2 by addition of a concentrated HCl solution and the mixture is concentrated under vacuum. The resulting product is used as is in the next stage.

F) (3S)-4-Benzyl-N,N-dimethylmorpholine-3-carboxamide.

9.81 g of PyBOP and then 10 ml of DIPEA are added at AT to a mixture of the compound obtained in the preceding stage in 20 ml of DCM and the mixture is left stirring for 30 minutes at AT. Dimethylamine gas is then added by bubbling for 10 minutes and the mixture is left stirring for 18 hours at AT. The reaction mixture is concentrated under vacuum, the residue is extracted with AcOEt, the organic phase is washed with an aqueous 5% $Na_2CO_3$ solution, with a saturated NaCl solution, dried over $MgSO_4$ and the solvent is concentrated under vacuum. The residue is chromatographed on silica gel, elution being carried out with a DCM/MeOH (98/2; v/v) mixture. 1.85 g of the expected product are obtained.

G) (3S)-N,N-Dimethylmorpholine-3-carboxamide.

A mixture of 1.83 g of the compound obtained in the preceding stage and 0.09 g of 10% palladium on carbon in 50 ml of EtOH is hydrogenated at 30° C. and at atmospheric pressure. The catalyst is filtered through Celite® and the filtrate is concentrated under vacuum. 1 g of the expected product is obtained.

$^1$H NMR: DMSO-$d_6$: δ(ppm) 2.85: s: 3H; 3.5: s: 3H; 3.2: mt: 2H; 3.3 to 4.3: up: 4H; 4.6: mt: 1H.

Preparations of the compounds of formula (II)

Preparation 3.1

(3S)-4-[5-Chloro-3-(2-methoxyphenyl)-2-oxo-2,3-dihydro-1H-indol-3-yl]-N,N-dimethylmorpholine-3-carboxamide, mixture of diastereoisomers.

(II): $R_1$=Cl; $R_2$=H; $R_3$=OCH$_3$; $R_4$=H; $R_5$=—N(CH$_3$)$_2$.

1.75 g of the compound obtained in Preparation 1.1 and then 0.8 ml of triethylamine are added at AT to a solution of 0.9 g of the compound obtained in Preparation 2.1 in 25 ml of DCM and the mixture is left stirring for 48 hours at AT. The reaction mixture is concentrated under vacuum, the residue is extracted with AcOEt, the organic phase is washed with an aqueous 5% $KHSO_4$ solution, with an aqueous 5% $Na_2CO_3$ solution, with a saturated NaCl solution, dried over $MgSO_4$ and the solvent is evaporated under vacuum. The residue is chromatographed on silica gel, elution being carried out with a DCM/MeOH (98/5; v/v) mixture. 1.63 g of the expected product are obtained.

$^1$H NMR: DMSO-$d_6$: δ(ppm): 2.0 to 2.8: up: 6H; 3.3: 2s: 3H; 3.4 to 4.2: up: 7H; 6.4 to 8.0: mt: 7H; 10.0 to 10.5: 2s: 1H.

Preparations 3.2 and 3.3

(3S)-4-[6-Chloro-3-(2-methoxyphenyl)-5-methyl-2-oxo-2,3-dihydro-1H-indol-3-yl]-N,N-dimethylmorpholine-3-carboxamide, isomer A and isomer B.

(II): $R_1$=CH$_3$; $R_2$=6-Cl; $R_3$=OCH$_3$; $R_4$=H; $R_5$=—N(CH$_3$)$_2$.

1.02 g of the compound obtained in Preparation 2.1 and then 0.7 ml of triethylamine are added at AT to a solution of 0.62 g of the compound obtained in Preparation 1.2 in 40 ml of DCM and the mixture is left stirring for 18 hours at AT. The reaction mixture is concentrated under vacuum, the residue is extracted with AcOEt, the organic phase is washed with an aqueous 5% $KHSO_4$ solution, with an aqueous 5% $Na_2CO_3$ solution, with a saturated NaCl solution, dried over $MgSO_4$ and the solvent is evaporated under vacuum. The residue is chromatographed over alumina, elution being carried out with a DCM/MeOH (99/1; v/v) mixture. The two isomers are separated:

the less polar, isomer A: compound of Preparation 3.2 which is crystallized from a DCM/iso ether mixture and 0.4 g is obtained, M.p.=237° C. $\alpha_D^{25}$=+106° (c=0.1; chloroform).

$^1$H NMR: DMSO-$d_6$: δ(ppm): 2.1: bs: 3H; 2.5 to 2.9: 2s: 6H; 3.3 to 4.2: up: 10H; 6.4: bs: 1H; 6.7: bs: 1H; 6.8: d: 1H; 7.0: t: 1H; 7.2: t: 1H; 7.9: d: 1H; 10.2: s: 1H.

the more polar, isomer B: compound of Preparation 3.3 which is crystallized from a DCM/iso ether mixture and 0.73 g is obtained, M.p.=177° C. $\alpha_D^{25}$=−150° (c=0.1; chloroform).

$^1$H NMR: DMSO-$d_6$: δ(ppm) : 2.0: s: 3H; 2.2 to 2.6: 2s: 6H; 3.4: s: 3H; 3.5 to 3.8: mt: 6H; 4.0: mt: 1H; 6.5: s: 1H; 6.7: s: 1H; 6.8: d: 1H; 7.0: t: 1H; 7.2: t: 1H; 7.8: d:,1H; 10.0: s: 1H.

Preparations 3.4 and 3.5

(3S)-4-[5-Chloro-3-(2-methoxyphenyl)-6-methyl-2-oxo-2,3-dihydro-1H-indol-3-yl]-N,N-dimethylmorpholine-3-carboxamide, isomer A and isomer B.

(II): $R_1$=Cl; $R_2$=6-CH$_3$; $R_3$=OCH$_3$; $R_4$=H; $R_5$=—N(CH$_3$)$_2$.

1.13 g of DIPEA are added to a mixture of 1.4 g of the compound obtained in Preparation 1.3 and 0.7 g of the compound obtained in Preparation 2.1 in 15 ml of DCM and the mixture is left stirring for 3 hours at AT. 0.65 g of DIPEA is added, the mixture is left stirring for 48 hours at AT and the formation of a precipitate is observed. The reaction mixture is concentrated under vacuum, the residue is taken up in an aqueous 5% $Na_2CO_3$ solution, extracted twice with AcOEt, the organic phase is washed with water, with a saturated NaCl solution, the precipitate present in the organic phase corresponding to isomer A, less polar compound, is filtered over aluminum, DCM/MeOH (95/5; v;v) (compound of Preparation 3.4). The filtration liquors are chromatographed on alumina, elution being carried out with a DCM/MeOH (95/5) mixture. The two isomers are separated:

the less polar, isomer A: compound of Preparation 3.4 which is added to the product previously obtained and crystallized from a DCM/AcOEt/MeOH mixture to obtain 0.292 g, M.p.=230–238° C. $\alpha_D^{25}$=+79.6° (c=0.1; chloroform).

the more polar, isomer B: compound of Preparation 3.5 and 0.887 g is obtained. $\alpha_D^{25}$=−100° (c=0.1; chloroform).

EXAMPLES 1 AND 2

(3S)-4-[5-Chloro-1-[(2,4-dimethoxyphenyl)sulfonyl]-3-(2-methoxyphenyl)-2-oxo-2,3-dihydro-1H-indol-3-yl]-N,N-dimethylmorpholine-carboxamide, isomer A and isomer B.

(I): $R_1$=Cl; $R_2$=H; $R_3$=OCH$_3$; $R_4$=H; $R_5$=—N(CH$_3$)$_2$; $R_6$=2-OCH$_3$; $R_7$=OCH$_3$.

A mixture of 1.85 g of the compound obtained in Preparation 3.1 in 18 ml of DMF is cooled to 4° C. under a nitrogen atmosphere, 0.191 g of 60% sodium hydride in oil is added and the mixture is left stirring for 30 minutes at 4° C. 1.02 g of 2,4-dimethoxybenzenesulfonyl chloride are then added and the mixture is left stirring for 3 hours at AT. 50 ml of water are added to the reaction mixture, it is extracted with AcOEt, the organic phase is washed with water, with a saturated NaCl solution, dried over MgSO$_4$ and the solvent is evaporated under vacuum. The residue is chromatographed on silica gel, elution being carried out with a DCM/MeOH (98/2; v/v) mixture. The two isomers are separated:

the less polar, isomer A: compound of Example 1 which is crystallized from hexane and 0.437 g is obtained, M.p.=156° C. $\alpha_D^{25}$=+136° (c=0.1; chloroform).

$^1$H NMR: DMSO-d$_6$: δ(ppm): 2.1 to 2.7: up: 8H; 2.9: bs: 3H; 3.6 to 4.2: up+2s: 11H; 6.7: up: 4H; 7.1: t: 1H; 7.3: td: 1H; 7.4: dd: 1H; 7.8: d: 1H; 7.9: d+up: 2H.

the more polar, isomer B: compound of Example 2 which is crystallized from a DCM/iso ether mixture and 0.7 g is obtained, M.p.=164° C. $\alpha_D^{25}$=−204° (c=0.1; chloroform).

$^1$H NMR: DMSO-d$_6$: δ(ppm): 2.5: bs: 6H; 3.1 to 3.7: up+s: 10H; 3.7 to 4.0: 2s: 6H; 6.5 to 6.8: 2up: 3H; 6.9: d: 1H; 7.1: t: 1H; 7.3: t: 1H; 7.5: dd: 1H; 7.8: d: 1H; 7.9: d: 1H; 8.1: bs: 1H.

EXAMPLE 3

(3S)-4-[6-Chloro-1-[(2,4-dimethoxyphenyl)sulfonyl]-3-(2-methoxyphenyl)-5-methyl-2-oxo-2,3-dihydro-1H-indol-3-yl]-N,N-dimethylmorpholine-3-carboxamide, levorotatory isomer.

(I): $R_1$=CH$_3$; $R_2$=6-Cl; $R_3$=OCH$_3$; $R_4$=H; $R_5$=—N(CH$_3$)$_2$; $R_6$=2-OCH$_3$; $R_7$=OCH$_3$.

A mixture of 0.61 g of the compound obtained in Preparation 3.3 (isomer B) in 5 ml of DMF is cooled to 4° C. under a nitrogen atmosphere, 0.06 g of 60% sodium hydride in oil is added and the mixture is left stirring for 30 minutes at AT. 0.36 g of 2,4-dimethoxybenzenesulfonyl chloride is then added and the mixture is left stirring for 2 hours at AT. 50 ml of water are added to the reaction mixture, it is extracted with AcOEt, the organic phase is washed with an aqueous 5% Na$_2$CO$_3$ solution, with a saturated NaCl solution, dried over Na$_2$SO$_4$ and the solvent is evaporated under vacuum. The residue is chromatographed on silica gel, elution being carried out with a DCM/AcOEt (70/30; v/v) mixture. 0.33 g of the expected product is obtained after crystallization from a DCM/iso ether mixture, M.p.=159° C. $\alpha_D^{25}$=−226° (c=0.1; chloroform).

$^1$H NMR: DMSO-d$_6$: δ(ppm): 2.0: s: 3H; 2.1 to 2.9: up: 11H; 3.6 to 4.0: up: 11H; 6.6: mt: 3H; 6.9: t: 1H; 7.1: t: 1H; 7.9 to 8.0: mt: 3H

EXAMPLE 4

(3S)-4-[5-Chloro-1-[(2,4-dimethoxyphenyl)sulfonyl]-3-(2-methoxyphenyl)-6-methyl-2-oxo-2,3-dihydro-1H-indol-3-yl]-N,N-dimethylmorpholine-3-carboxamide, levorotatory isomer.

(I): $R_1$=Cl; $R_2$=6-CH$_3$; $R_3$=OCH$_3$; $R_4$=H; $R_5$=—N(CH$_3$)$_2$; $R_6$=2-OCH$_3$; $R_7$=OCH$_3$.

A mixture of 0.875 g of the compound obtained in Preparation 3.5 (isomer B) in 8 ml of DMF is cooled to 0° C. under an argon atmosphere, 0.09 g of 60% sodium hydride in oil is added and the mixture is left stirring until the gaseous emission ceases. 0.49 g of 2,4-dimethoxybenzenesulfonyl chloride is then added and the mixture is left stirring for 3 hours at AT. The reaction mixture is poured into water, extracted with AcOEt, the organic phase is washed with water, with a saturated NaCl solution, dried over Na$_2$SO$_4$ and the solvent is evaporated under vacuum. The residue is chromatographed on silica gel, elution being carried out with a DCM/MeOH (97/3; v/v) mixture. 1.02 g of the expected product are obtained after crystallization from a DCM/iso ether mixture, M.p.=215–219° C. $\alpha_D^{25}$=−143.4° (c=0.11; chloroform).

What is claimed is:

1. A compound of formula:

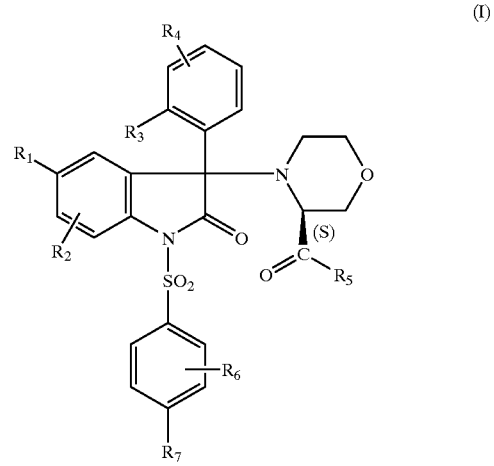

in which:

$R_1$ represents a halogen atom; a (C$_1$–C$_4$)alkyl; a (C$_1$–C$_4$) alkoxy; a trifluoromethyl radical; or a trifluoromethoxy radical;

$R_2$ represents a hydrogen atom; a halogen atom; a (C$_1$–C$_4$)alkyl; a (C$_1$–C$_4$)alkoxy; or a trifluoromethyl radical;

or else $R_2$ is in the 6-position of the indol-2-one ring and $R_1$ and $R_2$ together represent the bivalent trimethylene radical;

$R_3$ represents a halogen atom; a hydroxyl; a (C$_1$–C$_2$)alkyl; a (C$_1$–C$_2$)alkoxy; or a trifluoromethoxy radical;

$R_4$ represents a hydrogen atom; a halogen atom; a (C$_1$–C$_2$)alkyl; or a (C$_1$–C$_2$)alkoxy;

or else $R_4$ is in the 3-position of the phenyl and $R_3$ and $R_4$ together represent the methylenedioxy radical;

$R_5$ represents an ethylamino group; a dimethylamino group; an azetidin-1-yl radical; or a (C$_1$–C$_2$)alkoxy;

$R_6$ represents a (C$_1$–C$_4$)alkoxy;

$R_7$ represents a (C$_1$–C$_4$)alkoxy; or a solvate or hydrate thereof.

2. A compound according to claim 1 wherein the carbon atom in the 3-position of the indol-2-one has either the (R) configuration or the (S) configuration.

3. A compound according to claim 2, in the form of a levorotatory isomer.

4. The levorotatory isomer of (3S)-4-[5-chloro-1-[(2,4-dimethoxyphenyl)sulfonyl]-3-(2-methoxyphenyl)-2-oxo-2,3-dihydro-1H-indol-3-yl]-N,N-dimethylmorpholine-3-carboxamide or a solvate or hydrate thereof.

5. The levorotatory isomer of (3S)-4-[6-chloro-1-[(2,4-dimethoxyphenyl)sulfonyl]-3-(2-methoxyphenyl)-5-methyl-2-oxo-2,3-dihydro-1H-indol-3-yl]-N,N-dimethylmorpholine-3-carboxamide or a solvate or hydrate thereof.

6. The levorotatory isomer of (3S)-4-[5-chloro-1-[(2,4-dimethoxyphenyl)sulfonyl]-3-(2-methoxyphenyl)-6-methyl-2-oxo-2,3-dihydro-1H-indol-3-yl]-N,N-dimethylmorpholine-3-carboxamide or a solvate or hydrate thereof.

7. A process for the preparation of a compound according to claim 1, wherein:

a compound of formula:

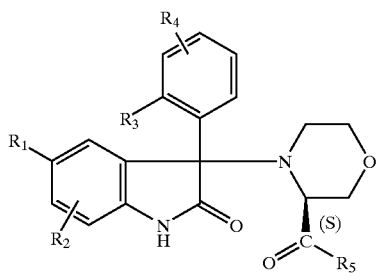

is reacted, in the presence of a base, with a halide of formula:

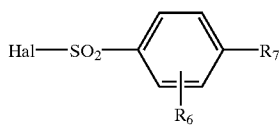

in which $R_1$, $R_2$, $R_3$, $R_4$, $R_5$, $R_6$ and $R_7$ are as defined in claim 1 and Hal represents a halogen atom.

8. A compound of formula:

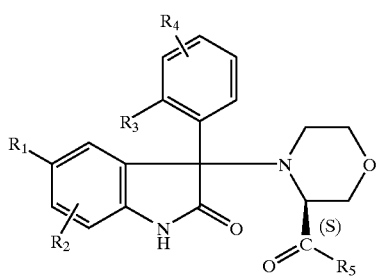

in which:
- $R_1$ represents a halogen atom; a $(C_1-C_4)$alkyl; a $(C_1-C_4)$alkoxy; a trifluoromethyl radical; or a trifluoromethoxy radical;
- $R_2$ represents a hydrogen atom; a halogen atom; a $(C_1-C_4)$alkyl; a $(C_1-C_4)$alkoxy; or a trifluoromethyl radical;
- or else $R_2$ is in the 6-position of the indol-2-one ring and $R_1$ and $R_2$ together represent the bivalent trimethylene radical;
- $R_3$ represents a halogen atom; a hydroxyl; a $(C_1-C_2)$alkyl; a $(C_1-C_2)$alkoxy; or a trifluoromethoxy radical;
- $R_4$ represents a hydrogen atom; a halogen atom; a $(C_1-C_2)$alkyl; or a $(C_1-C_2)$alkoxy;
- or else $R_4$ is in the 3-position of the phenyl and $R_3$ and $R_4$ together represent the methylenedioxy radical;
- $R_5$ represents an ethylamino group; a dimethylamino group; an azetidin-1-yl radical; or a $(C_1-C_2)$alkoxy; or an acid addition salt thereof.

9. A pharmaceutical composition comprising a compound according to claim 1 and a pharmaceutically acceptable excipient.

10. A compound according to claim 3 wherein:
- $R_1$ is chloro or methyl;
- $R_2$ is hydrogen or is in the 6-position of the indol-2-one and is chloro or methyl;
- $R_3$ is methoxy;
- $R_4$ is hydrogen;
- $R_5$ is dimethylamino;
- $R_6$ is in the 2-position of the phenyl and is methoxy; and
- $R_7$ is methoxy.

11. A pharmaceutical composition comprising a compound according to claim 4 and a pharmaceutically acceptable excipient.

12. A pharmaceutical composition comprising a compound according to claim 5 and a pharmaceutically acceptable excipient.

13. A pharmaceutical composition comprising a compound according to claim 6 and a pharmaceutically acceptable excipient.

14. A pharmaceutical composition comprising a compound according to claim 10 and a pharmaceutically acceptable excipient.

15. A method for the treatment of a disease in which arginine-vasopressin or its $V_{1b}$ receptors or both its $V_{1b}$ and $V_{1a}$ receptors are involved which comprises administering to a patient in need of such treatment an effective amount of a compound according to claim 1.

16. A method for the treatment of a disease in which arginine-vasopressin or its $V_{1b}$ receptors or both its $V_{1b}$ and $V_{1a}$ receptors are involved which comprises administering to a patient in need of such treatment an effective amount of a compound according to claim 4.

17. A method for the treatment of a disease in which arginine-vasopressin or its $V_{1b}$ receptors or both its $V_{1b}$ and $V_{1a}$ receptors are involved which comprises administering to a patient in need of such treatment an effective amount of a compound according to claim 5.

18. A method for the treatment of a disease in which arginine-vasopressin or its $V_{1b}$ receptors or both its $V_{1b}$ and $V_{1a}$ receptors are involved which comprises administering to a patient in need of such treatment an effective amount of a compound according to claim 6.

19. A method for the treatment of a disease in which arginine-vasopressin or its $V_{1b}$ receptors or both its $V_{1b}$ and $V_{1a}$ receptors are involved which comprises administering to a patient in need of such treatment an effective amount of a compound according to claim 10.

20. A method according to claim 15 for the treatment of disorders of the central nervous system.

21. A method according to claim 16 for the treatment of disorders of the central nervous system.

22. A method according to claim 17 for the treatment of disorders of the central nervous system.

23. A method according to claim 18 for the treatment of disorders of the central nervous system.

24. A method according to claim 19 for the treatment of disorders of the central nervous system.

* * * * *